United States Patent [19]

Sitzmann

[11] Patent Number: 5,274,103

[45] Date of Patent: Dec. 28, 1993

[54] 1,3,4-OXADIAZOLES CONTAINING THE PENTAFLUOROTHIO (SF5) GROUP

[75] Inventor: Michael E. Sitzmann, Adelphi, Md.

[73] Assignee: The United States of America as represented by the Secretary of the Navy, Washington, D.C.

[21] Appl. No.: 59,768

[22] Filed: May 10, 1993

[51] Int. Cl.⁵ .......................................... C07D 271/10
[52] U.S. Cl. ..................................................... 548/143
[58] Field of Search ........................................ 548/143

[56] References Cited

U.S. PATENT DOCUMENTS

| | | | |
|---|---|---|---|
| 4,740,628 | 4/1988 | Adolph et al. | 568/603 |
| 5,214,189 | 5/1993 | Sitzmann | 558/482 |
| 5,241,071 | 8/1993 | Sitzmann | 548/143 |

Primary Examiner—Robert W. Ramsuer
Assistant Examiner—Joseph K. McKane
Attorney, Agent, or Firm—John D. Lewis; Roger D. Johnson

[57] ABSTRACT

1,3,4-Oxadiazoles of the formula

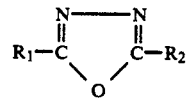

are prepared by cyclization (dehydration) of the corresponding diacylhydrazines of the formula $R_1C(O)NHNHC(O)R_2$ with phosphorous pentachloride or phosphorous oxychloride wherein $R_1$ is $-CF_2CF_2CF_2SF_5$, $-CF_2CF_2SF_5$, or $-CH_2SF_5$ and $R_2$ is $-CH_2CH_2C(NO_2)_3$, $-CH_2CH_2C(NO_2)_2F$, $-CF_2CF_2CF_3$, $-CF_2CF_3$, $-CF_3$, or $-CH_2SF_5$. The compounds are useful as plasticizers.

8 Claims, No Drawings

1,3,4-OXADIAZOLES CONTAINING THE PENTAFLUOROTHIO (SF₅) GROUP

BACKGROUND OF THE INVENTION

This invention relates to plasticizers and more particularly to energetic plasticizers for plastic bonded explosives.

A number of new fluorinated binders [for example, perfluoroalkyl polyformals as described by H. G. Adolph and J. M. Goldwasser; U.S. Pat. No. 4,740,579 (1988) and U.S. Pat. No. 4,740,628 (1988)] have recently become available and energetic formulations that contain these new fluorinated binders along with nitro oxidizers/explosives (HMX, for example) have been prepared. These new highly fluorinated binders exhibit quite different chemical properties compared to the nitro oxidizers/explosives. Because of these differences in properties, the usual nitro plasticizers (FEFO, NG, TMETN) used in the formulations are attracted toward the nitro oxidizer/explosive and not the fluorinated binder. These differences in the attraction of the nitro plasticizer for the binder and oxidizer can cause the plasticizer to migrate during storage of the formulations. U.S. patent application Ser. No. 07/901,621, now U.S. Pat. No. 5,241,071 filed on Jun. 15, 1992 by Michael E. Sitzmann (identical to the current inventorship) discloses 2-polynitroalkyl-5-perfluoroalkyl-1,3,4-oxadiazole plasticizers which solve the migration problem.

It would be desirable to provide low melting plasticizers which do not migrate in fluoropolymer/nitroexplosive composites and which possess low melting points but which have lower volatilities but greater densities and energies than the 2-polynitroalkyl-5-perfluoroalkyl-1,3,4-oxadiazoles. Moreover, it would be desirable to provide plasticizers which possess the general properties (such as low melting points) of conventional fluoroplasticizers but which are less volatile and more dense and energetic than the conventional fluoroplasticizers.

SUMMARY OF THE INVENTION

Accordingly, an object of this invention is to provide new energetic plasticizers.

Another object of this invention is to provide new energetic plasticizers that are attracted to both nitro compounds and fluoro compounds.

A further object of this invention is to provide energetic fluoroplasticizers with lowered volatility.

Still another object is to provide energetic plasticizers with greater density and thus greater energy content.

These and other objects of this invention are accomplished by providing:

energetic 1,3,4-oxadiazoles of the formula

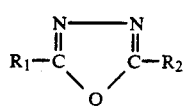

wherein $R_1$ is $SF_5CF_2CF_2CF_2-$, $SF_5CF_2CF_2-$, or $SF_{CH2}-$, and $R_2$ is $-CH_2CH_2C(NO_2)_3$, $-CH_2CHCF(NO_2)_2$, $-CH_2SF_5$, $-CF_2CF_2CF_3$, $-CF_2CF_3$, or $-CF_3$.

DETAILED DESCRIPTION OF THE PREFERRED EMBODIMENT

These energetic 1,3,4-oxadiazole compounds of this invention may be represented by the formula

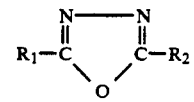

wherein $R_1$ is $SF_5CF_2CF_2CF_2-$, $SF_5CF_2CF_2-$, or $SF_5CH_2-$, and $R_2$ is $-CH_2CH_2C(NO_3)_3$, $-CH_2CH_2CF(NO_2)_2$, $-CH_2SF_5$, $-CF_2CF_2CF_3$, $-CF_2CF_3$, or $-CF_3$.

Specifically the preferred energetic 1,3,4-oxadiazole compounds are:

(1) 2-(3-pentafluorothioperfluoropropyl)-5-(3,3,3-trinitropropyl)-1,3,4-oxadiazole,

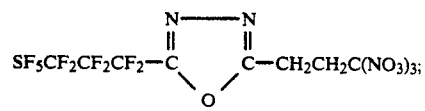

(2) 2-(2-pentafluorothioperfluoroethyl)-5-(3,3,3-trinitropropyl)-1,3,4-oxadiazole,

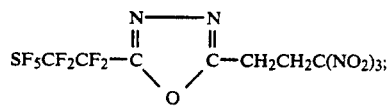

(3) 2-(3-pentafluorothioperfluoropropyl)-5-(3-fluoro-3,3-dinitropropyl)-1,3,4-oxadiazole,

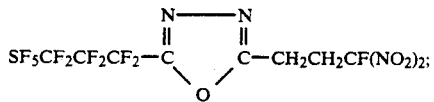

(4) 2-(2-pentafluorothioperfluoroethyl)-5-(3-fluoro-3,3-dinitropropyl)-1,3,4-oxadiazole,

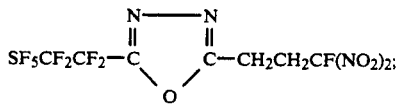

(5) 2-(3-pentafluorothioperfluoropropyl)-5-(pentafluorothiomethyl)-1,3,4-oxadiazole,

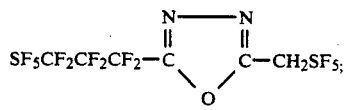

(6) 2-(2-pentafluorothioperfluoroethyl)-5-(pentafluorothiomethyl)-1,3,4-oxadiazole,

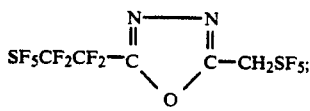

(7) 2-(pentafluorothiomethyl)-5-(3,3,3-trinitropropyl)-1,3,4-oxadiazole,

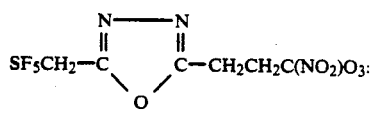

(8) 2-(pentafluorothiomethyl)-5-(3-fluoro-3,3-dinitropropyl)-1,3,4-oxadiazole,

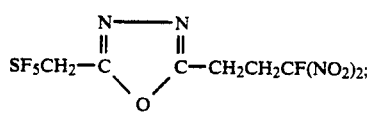

(9) 2-(pentafluorothiomethyl)-5-(perfluoropropyl)-1,3,4-oxadiazole,

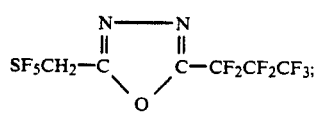

(10) 2-(pentafluorothiomethyl)-5-(perfluoroethyl)-1,3,4-oxadiazole,

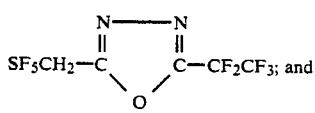

(11) 2-(pentafluorothiomethyl)-5-(trifluoromethyl)-1,3,4-oxadiazole,

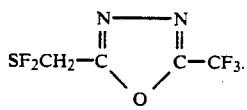

The 1,3,4-oxadiazoles (1) through (11) can be prepared by cyclization (dehydration) of the corresponding diacylhydrazines (1A) through (17A), respectively. Specifically the diacylhydrazines are:

(1A) N-(4-pentafluorothioperfluorobutyryl)-N'-(4,4,4-trinitrobutyryl)hydrazine,
$SF_5CF_2CF_2CF_2C(O)NHNHC(O)CH_2CH_2C(NO_2)_3$;

(2A) N-(3-pentafluorothioperfluoropropionyl)-N'-(4,4,4-trinitrobutyryl)hydrazine,
$SF_5CF_2CF_2C(O)NHNHC(O)CH_2CH_2C(NO_2)_3$;

(3A) N-(4-pentafluorothioperfluorobutyryl)-N'-(4-fluoro-4,4-dinitrobutyryl)hydrazine,
$SF_5CF_2CF_2CF_2C(O)NHNHC(O)CH_2CH_2CF(NO_2)_2$;

(4A) N-(3-pentafluorothioperfluoropropionyl)-N'-(4-fluoro-4,4-dinitrobutyryl)hydrazine,
$SF_5CF_2CF_2C(O)NHNHC(O)CH_2CH_2CF(NO_2)_2$;

(5A) N-(4-pentafluorothioperfluorobutyryl)-N'-(pentafluorothioacetyl)hydrazine,
$SF_5CF_2CF_2CF_2C(O)NHNHC(O)CH_2SF_5$;

(6A) N-(3-pentafluorothioperfluoropropionyl)-N'-(pentafluorothioacetyl)hydrazine,
$SF_5CF_2CF_2C(O)NHNHC(O)CH_2SF_5$;

(7A) N-(pentafluorothioacetyl)-N'-(4,4,4-trinitrobutyryl)hydrazine, $SF_5CH_2C(O)NHNHC(O)CH_2CH_2C(NO_2)_3$;

(8A) N-(pentafluorothioacetyl)-N'-(4-fluoro-4,4-dinitrobutyryl)hydrazine, $SF_5CH_2C(O)NHNHC(O)CH_2CH_2CF(NO_2)_2$;

(9A) N-(pentafluorothioacetyl)-N'-(perfluorobutyryl)hydrazine, $SF_5CH_2C(O)NHNHC(O)CF_2CF_2CF_3$;

(10A) N-(pentafluorothioacetyl)-N'-(perfluoropropionyl)hydrazine, $SF_5CH_2C(O)NHNHC(O)CF_2CH_3$; and (11A) N-(pentafluorothioacetyl)-N'-(trifluoroacetyl)hydrazine, $SF_5CH_2C(O)NHNHC(O)CF_3$.

For diacylhydrazines (1A) through (4A) where the pentafluorothioacetyl group, $SF_5CH_2CO$), is absent, the cyclization (dehydration) can be achieved by refluxing the selected diacylhydrazine either with phosphorous pentachloride, $PCl_5$, in a suitable solvent such as 1,2-dichloroethane, $ClCH_2CH_2Cl$, or with phosphorous oxychloride, $POCl_3$. However, refluxing the diacylhydrazines (5A) through (A), which contain a pentafluorothioacetyl group, with phosphorous pentachloride produces the dichloride rather than the desired 1,3,4-oxadiazoles (5) through (11). Example 16 illustrates this problem. Therefore, the diacylhydrazines (5A) through (11A) must be refluxed with phosphorous oxychloride to produce the desired 1,3,4-oxadiazoles (5) through (11) (See examples 10, 12, 14, and especially 16). Further details of the process are illustrated in the examples.

The diacylhydrazines (1A) through (11A) can be prepared by reacting equal molar amounts of a monoacylhydrazine that is (C1) N-(4-pentafluorothioperfluorobutyryl)hydrazine, $SF_5CF_2CF_2CF_2CO)NHNH_2$;

(C2) N-(3-pentafluorothioperfluoropropionyl)hydrazine, $SF_5CF_2CF_2CO)NHNH_2$;

(C3) N-(pentafluorothioacetyl)hydrazine, $SF_5CH_2C(O)NHNH_2$;

(C4) N-(perfluorobutyryl)hydrazine, $CF_3CF_2CF_2C(O)NHNH_2$;

(C5) N-(perfluoropropionyl)hydrazine, $CF_3CF_2C(O)NHNH_2$; or (C6) N-(trifluoroacetyl)hydrazine, $CF_3(O)NHNH_2$, with an acid chloride that is, (D1) 4,4,4-trinitrobutyryl chloride, $C(NO_2)_3CH_2CH_2C(O)Cl$;

(D2) 4-fluoro-4,4-dinitrobutyryl chloride, $CF(NO_2)_2CH_2CH_2C(O)Cl$; or (D3) pentafluorothioacetyl chloride, $SF_5CH_2C(O)Cl$, in the presence of pyridine.

Table 1 summarizes the monoacylhydrazine and acid chloride which can be used to produce each of the desired diacylhydrazines (1A) through (11A).

TABLE 1

| Product diacylhydrazine | Reactants | |
| --- | --- | --- |
| | monoacylhydrazine | acid chloride |
| 1A | C1 | D1 |
| 2A | C2 | D1 |
| 3A | C1 | D2 |

TABLE 1-continued

| Product diacylhydrazine | Reactants | |
|---|---|---|
| | monoacylhydrazine | acid chloride |
| 4A | C2 | D2 |
| 5A | C1 | D3 |
| 6A | C2 | D3 |
| 7A | C3 | D1 |
| 8A | C3 | D2 |
| 9A | C4 | D3 |
| 10A | C5 | D3 |
| 11A | C6 | D3 |

Equal molar mounts of the monoacylhydrazine and the acid chloride are dissolved in a suitable solvent such as diethyl ether at room temperature. Pyridine is slowly added to the solution until the molar amount of pyridine slightly exceeds that of the monoacrylhydrazine and acid chloride. Details of the process are illustrated by examples 3, 5, 7, 9, 11, 13, 15, and 17.

A method for preparing mono(acryl)hydrazines such as N-(perfluorobutyryl)hydrazine, $CF_3CF_2CF_2C(O)NHNH_2$, by treating esters [$R_fC(O)OR$] with hydrazine, has been reported [H. C. Brown, M. T. Cheng, L. J. Parcell, and D. Pilipovich, J. Org. Chem., 26, 407 (1961)]. The previously unknown compounds, N-(4-pentafluorothioperfluorobutyryl)hydrazine (see example 1) and N-(3-pentafluorothioperfluoropropionyl)hydrazine (see example 2) were prepared similarly in good yields but numerous attempts to prepare $SF_5CF_2C(O)NHNH_2$ from $SF_5CF_2C(O)OCH_3$ gave only decomposition reactions instead of the desired mono(acyl)hydrazine. Significant decomposition occurred during a similar reaction to produce N-(pentafluorothioacetyl)hydrazine. However, although N-(pentafluorothioacetyl)hydrazine was not isolated in the pure state from this reaction, it was successfully condensed with an acyl halide (see example 15). N-(pentafluorothioacetyl)hydrazine could not be prepared from $SF_5CF_2C(O)Cl$ and hydrazine, a reaction which yielded mainly the bis(acyl)hydrazine: bis(pentafluorothioacetyl)hydrazine (see example 19).

The preparation of perfluoroacyl hydrazines, $CF_3(CF_2)_nC(=O)NHNH_2$, have been described by H. C. Brown et al., Journal of Organic Chemistry, 26(11), P. 4407 (1961), herein incorporated in its entirety. Their procedures were repeated to produce $CF_3CF_2C(=O)NHNH_2$ and $CF_3CF_2CF_2C(=O)NHNH_2$. For $CF_3(C=O)NHNH_2$, they report a melting point of 143°-144° C. but this is apparently an error. The melting point for this compound was found to be 42°-43° C. and was prepared as follows: To 4.5 g (0.032 mole) of ethyl trifluoroacetate stirred in an ice bath was added 1.0 g (0.032 mole) of anhydrous hydrazine (95% min) in 3 mL of methanol. After 16 hours at room temperature, methylene chloride (15 mL) was added and the volatiles were removed by distillation (bath temperature was eventually raised to 100° C. and held until distillation stopped). After cooling, 30 mL of methylene chloride was added and the mixture was stirred to produce an insoluble solid. The solid (mp 128°-133° C.) was removed and the filtrate was cooled to −20° C. to give 1.7 g, mp 35°-38° C. Recrystallization from methylene chloride gave 1.1 g of N-(trifluoacetyl)hydrazine, mp 42°-43° C.

The 4,4,4-trinitrobutyryl chloride (Chemical Abstract Number 36638-86-5) starting material was prepared by refluxing 4,4,4-trinitrobutyric acid with an excess of thionyl chloride for 20 hours before the mixture was concentrated in vacuo and the product distilled as taught by Marvin H. Gold, et al. in an article titled, "Preparation of Aliphatic gem-Dinitro Monoisocyanates and Derivatives," Journal of Organic Chemistry (1962), volume 27, pages 334-335, at page 334, column 2, herein incorporated by reference in its entirety.

The 4-fluoro-4,4-trinitrobutyryl chloride starting material can be prepared in a similar manner. 4-Fluoro-4,4-dinitrobutyric acid is added in portions with stirring to an excess of thionyl chloride at 18°-20° C. The homogeneous solution formed is then heat slowly to boiling where it is kept for about 2 hours. The excess thionyl chloride is then distilled off. The 4-fluoro-4,4-trinitrobutyryl chloride product is then distilled off under vacuum. This procedure was taught by L. T. Eeremenko et al. Izvestlya Akademil Nauk SSR, Seriya Khimicheskaya No. 6, pp 1331-1336 June, 1969.

A method of preparing pentafluorothioacetyl chloride, $SF_5CH_2COCl$, is disclosed in example II, column 5, of U.S. Pat. No. 3,102,903, which is herein incorporated by reference in its entirety.

A number of 1,3,4-oxadiazoles, containing perfluoroalkyl [$CF_3(CF_2)_n$] and polynitroalkyl groups, were recently disclosed in U.S. patent application Serial No. 07/901,623, now U.S. Pat. No. 5,214,189 filed on Jun. 15, 1992 by Michael E. Sitzmann for use as energetic plasticizers in formulations containing nitro oxidizers and fluorinated binders. The substitution of an $SF_5(CF_2)n$ group for $CF_3(CF_2)_n$ in these oxadiazoles will generally produce little change in the melting points (see Table 2). This suggests that the $SF_5(CF_2)_n$ compounds

TABLE 2

Comparison of the Melting Points of 1,3,4-oxadiazoles, $R_1R_2(C_2N_2O)$, for $R_1 = SF_5(CF_2)_2$ vs. $R_1 = CF_3(CF_2)_2$

| $R_1$ | $R_2$ | m.p. °C. |
|---|---|---|
| $SF_5(CF_2)_2$ | $CH_2CH_2C(NO_2)_2F$ | 22 |
| $CF_3(CF_2)_2$ | $CH_2CH_2C(NO_2)_2F$ | 21 |
| $SF_5(CF_2)_2$ | $CH_2SF_5$ | 27 |
| $CF_3(CF_2)_2$ | $CH_2SF_5$ | 28 |

This suggests that the $SF_5(CF_2)_n$ compounds will be similar to the $CF_3(CF_2)n$ compounds regarding their use as energetic plasticizers. However, the $SF_5$ materials will offer an advantage in that they will be less volatile (compare the boiling points of $SF_5CF_2CO_2H$ and $CF_3CF_2CO_2H$ [150° C. and 98° C., respectively]). In addition, the $SF_5(CF_2)_n$ compounds will have higher densities which is an advantage since detonation pressure is related to the square of the density. As an example, 2-(2-pentafluorothioperfluoroethyl)-5-(3-fluoro-3,3-dinitropropyl)-1,3,4-oxadiazole (4) [$R_1=SF_5(CF_2)_2$ and $R_2=CH_2CH_2C(NO_2)_2F$] has a calculated density of 1.76 g/cc (actual liquid density measured to be 1.80 g/cc) which is significantly higher than the density (1.59 g/cc) calculated for the analogous perfluoroalkyl compound [$R_1=CF_3(CF)_2$ and $R_2=CH_2CH_2C(NO_2)_2F$]. The densities are calculated according to D. A. Cichra, J. R. Holden and C. Dickinson in "Estimation of Normal Densities of Explosive Compounds from Empirical Atomic Volumes," Naval Surface Warfare Center, NSWC TR 79-273, Silver Spring, Md., February 1980.

Furthermore, comparison of S—F and C—F bond energies (79 and 107 kcal/mole, respectively) indicates that the $SF_5(CF_2)_n$ oxadiazoles will provide more energy than the similar $CF_3(CF_2)_n$ materials, particularly in metalized compositions (for example, Al—F bond energy=158 kcal/mole). In other words, conversion of S—F to Al—F will be more exothermic than a similar conversion of C—F to Al—F.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1

N-(4-Pentafluorothioperfluorobutyryl)hydrazine (C1)

Crude 4-pentafluorothiobutyric acid was purified by treating an ether solution with pyridine to give the pyridine salt as an insoluble solid, mp 102°–104° C. Methyl 4-pentafluorothioperfluorobutyrate was formed by adding 9.0 g (0.0224 mole) of the pyridine salt to 9 ml of concentrated sulfuric acid stirred at 0° C., then adding 4.5 ml of methanol and heating the mixture at 80°–85° C. for 40 minutes. The cooled mixture was poured onto ice, and the aqueous mixture was extracted with diethyl ether. The ether extract was washed with water, then dried over $MgSO_4$ before the volatiles were removed. The residue which $^1H$ NMR ($CDCl_3$) showed to be essentially pure methyl ester ($OCH_3$ at 4.10 ppm) was stirred at 0° C. while 0.75 g (0.0234 mole) of hydrazine in 8 ml of methanol was added. After 2 hours at 25° C., the volatiles were removed and the residue was stirred with water to give 6.45 g (86%) of insoluble solid, mp 18°–83° C. Crystallization from dichloroethane gave 5.8 g (77%) of N-(4-pentafluorothioperfluorolbutyryl)hydrazine, mp 85°–86° C.; IR (KBr): 3360 (NH), 1700 (C=O), 1225–1140 (CF), 925–800 ($SF_5$). Anal. Calcd. for $C_4H_3F_{11}N_2OS$: C, 14.29; H, 0.90; F, 62.18; N, 8.33; S, 9.54. Found: C, 14.25; H, 0.87; F, 62.08; N, 8.39; S, 10.20.

EXAMPLE 2

N-(3-Pentafluorothioperfluoropropionyl)hydrazine (C2)

To 5.0 g (0.016 mole, 85% pure by $^{19}F$ NMR) of propyl 3-pentafluorothioperfluoropropionate stirred at 0° C. was added 0.51 g (0.016 mole) of hydrazine in 4.5 ml of methanol. After 3 hours at 25° C., dichloromethane (20 ml) was added and 0.1 g of insoluble solid was removed by filtration. The volatiles were removed from the filtrate (under reduced pressure) to give 4.4 g of oil which was extracted with 3×15 ml of warm dichloromethane (approx. 0.5 g of oil remained insoluble). The combined dichloromethane extracts were cooled to −20° C. to give 2.0 g (53%) of N-(3-pentafluorothioperfluoropropionyl)hydrazine, mp 66°–68° C. Recrystallization from dichloromethane yielded 1.8 g, mp 68°–70° C.; IR (KBr): 3320 (NH), 1725, 1705 (C=O), 1190–1135 (CF), 875–820 ($SF_5$).

EXAMPLE 3

N-(4-Pentafluorothioperfluorobutyryl)-N'-(4,4,4-trinitrobutyryl)hydrazine (1A)

Pyridine (0.3 ml, 0.0038 mole) was added dropwise to a mixture of 0.8 g (0.0033 mole) of 4,4,4-trinitrobutyryl chloride and 1.0 g (0.0030 mole) of N-(4-pentafluorothioperfluorobutyryl)hydrazine in 25 ml of diethyl ether stirred at 25° C. After 20 minutes, dilute hydrochloric acid was added and the ether layer was separated. Drying ($Na_2SO_4$), removal of volatiles and stirring the residue with water gave 1.45 g, mp 138°–144° C. Crystallization from 1,2-dichloroethane produced 1.05 g (65%) of N-(4-pentafluorothioperfluorobutyryl)-N'-(4,4,4-trinitrobutyryl)hydrazine, mp 153°–155° C.; $^1H$ NMR (acetone-$d_6$+$D_2O$): 2.95 (t, 2H), 3.83 (t, 2H); IR (KBr) 3250 (NH), 1740, 1670 (C=O), 1240–1115 (CF), 890–790 ($SF_5$). Anal. Calcd. for $C_8H_6F_{11}N_5O_8S$: C, 17.75; H, 1.12; F, 38.62; N, 12.94; S, 5.92. Found: C, 18.00; H, 1.18; F, 38.44; N, 12.73; S, 6.48.

EXAMPLE 4

2-(3-Pentafluorothioperfluoropropyl)-5-(3,3,3-trinitropropyl)-1,3,4-oxadiazole (1)

N-(4-Pentafluorothioperfluorobutyryl)-N'-(4,4,4-trinitrobutyryl)hydrazine (0.45 g, 0.83 mmole) and phosphorus pentachloride (0.65 g, 3.1 mmole) in 1,2-dichloroethane (6 ml) was held at reflux for 4 hours before the volatiles were removed. The residue was stirred with water before it was extracted into dichloromethane and chromatographed on Silica gel 40 ($CH_2Cl_2$ as eluent) to give 0.34 g (79%) of 2-(3-pentafluorothioperfluoropropyl)-5-(3,3,3-trinitropropyl)-1,3,4-oxadiazole, mp 54°–56° C.; $^1H$ NMR (acetone-$d_6$): 3.83 (m, 2H), 4.23 (m, 2H). IR (KBr): 1605 ($NO_2$), 1235–1140 (CF), 910–795 ($SF_5$). Anal Calcd. for $C_8H_4F_{11}N_5O_7S$: C, 18.36; H, 0.77; F, 39.94; N, 13.38; S, 6.13. Found: C, 18.34; H, 0.74; F, 37.55; N, 13.35; S, 6.16

EXAMPLE 5

N-(3-Pentafluorothioperfluoropropionyl)-N'-(4,4,4-trinitrobutyryl)hydrazine (2A)

To 0.85 g (0.0035 mole) of 4,4,4-trinitrobutyryl chloride in 25 ml of diethyl ether stirred at 25° C. was added 1.0 g (0.0035 mole) of N-(3-pentafluorothioperfluoropropionyl)hydrazine followed by the dropwise addition of 0.35 ml (0.004 mole) of pyridine After 10 minutes, dilute hydrochloric acid (10 ml) was added and the ether layer was separated and dried ($Na_2SO_4$) before the volatiles were removed to give a solid residue. Stirring the solid with water gave 1.68 g (98%) of insoluble solid, mp 167°–171° C. Crystallization from 1,2-dichloroethane gave 1.30 g of N-(3-pentafluorothioperfluoropropionyl)-N'-(4,4,4-trinitrobutyryl)hydrazine, mp 177°–178° C. dec.

EXAMPLE 6

2-(2-Pentafluorothioperfluoroethyl)-5-(3,3,3-trinitropropyl)-1,3,4-oxadiazole (2)

A mixture of 0.8 g (0.0016 mole) of N-(3-pentafluorothioperfluoropropionyl)-N'-(4,4,4-trinitrobutyryl)hydrazine, 1.1 g (0.005 mole) of phosphorus pentachloride and 10 ml of 1,2-dichloroethane was held at reflux temperature for 4.5 hours before it was cooled and washed with water. The volatiles were removed to give a residue (0.78 g) which was chromatographed on Silica gel 40 ($CH_2Cl_2$ as eluent) to give 0.57 g (74%) of 2-(2-pentafluorothioethyl)-5-(3,3,3-trinitropropyl)-1,3,4-oxadiazole, mp 54°–55° C. Anal. Calcd. for $C_7H_4F_9N_5O_7S$: C, 17.77; H, 0.85; F, 36.14; N, 14.80; S, 6.77. Found: C, 17.85: H, 0.85: F, 36.10: N, 14.70: S, 6.46.

EXAMPLE 7

N-(4-Pentafluorothioperfluorobutyryl)-N'-(4-fluoro-4,4-dinitrobutyryl)hydrazine (3A)

A mixture of 0.4 g (0.0018 mole) of 4-fluoro-4,4-dinitrobutyryl chloride and 0.5 g (0.0015 mole) of N-(4-pentafluorothioperfluorobutyryl)hydrazine in 15 ml of diethyl ether was stirred at 25° C. while 0.2 ml (0.0025 mole) of pyridine was added dropwise. Dilute hydrochloric acid was added, the ether layer was separated and dried ($Na_2SO_4$) and the volatiles were removed to give a solid that was washed with water and crystallized from 1,2-dichloroethane to yield 0.45 g (59%) of N-(4-pentafluorothioperfluorobutyryl)-N'-(4-fluoro-4,4-dinitrobutyryl)hydrazine, mp 121°–122° C.

EXAMPLE 8

2-(3-Pentafluorothioperfluoropropyl)-5-(3-fluoro-3,3-dinitropropyl)-1,3,4-oxadiazole (3)

A mixture containing 1,2-dichloroethane (5 ml), (4-pentafluorothioperfluorobutyryl)-N'-(4-fluoro-4,4-dinitrobutyryl)hydrazine (0.38 g, 0.77 mmole) and phosphorus pentachloride (0.6 g, 2.88 mmole) was held at reflux temperature for 4.5 hours before the solution was cooled and washed with water. Removal of volatiles gave a residue which was chromatographed (Silica gel 40, $CH_2Cl_2$ as eluent) to yield 0.18 g (50%) of 2-(3-pentafluorothioperfluoropropyl)-5-(3-fluoro-3,3-dinitropropyl)-1,3,4-oxadiazole, mp 36°–37° C. Anal. Calcd. for $C_8H_4F_{12}N_4O_5S$: C, 19.36; H, 0.81; F, 45.95; N, 11.29; S, 6.46. Found C, 19.35; H, 0.83; F, 45.61; N, 11.41; S, 6.44.

EXAMPLE 9

N-(3-Pentafluorothioperfluoropropionyl)-N'-(4-fluoro-4,4-dinitrobutyryl)hydrazine (4A)

To a mixture of 0.65 g (0.003 mole) of 4-fluoro-4,4-dinitrobutyryl chloride and 0.85 g (0.003 mole) of N-(3-pentafluorothioperfluoropropionyl)hydrazine in 25 ml of diethyl ether stirred at 25° C. was added 0.3 ml (0.0038 mole) of pyridine dropwise. After 10 minutes, 10 ml of dilute hydrochloric acid (10%) was added and the ether layer was separated and dried ($Na_2SO_4$). Removal of volatiles gave a residue which was stirred with water to yield 1.25 g (90%) of insoluble solid, mp 155°–162° C. Crystallization from 1,2-dichloroethane gave 0.92 g (66%) of N-(3-pentafluorothioperfluoropropionyl)-N'-(4-fluoro-4,4-dinitrobutyryl)hydrazine, mp 165°–167° C.

EXAMPLE 10

2-(2-Pentafluorothioperfluoroethyl)-5-(3-fluoro-3,3-dinitropropyl)-1,3,4-oxadiazole (4)

A mixture of 0.8 g (0.0017 mole) of N-(3-pentafluorothioperfluoropropionyl)-N-(4-fluoro-4,4-dinitrobutyryl)hydrazine, 1,1 g (0.005 mole) of phosphorus pentachloride and 10 ml of 1,2-dichloroethane was held at reflux for 4.5 hours. The mixture was cooled, washed with water and the volatiles removed to give a residue which was chromatographed on Silica gel 40 ($CH_2Cl_2$ as eluent) to give 0.55 g (72%) of 2-(2-pentafluorothioperfluoroethyl)-5-(3-fluoro-3,3-dinitropropyl)-1,3,4-oxadiazole, mp 22°–23° C.; $^1H$ NMR ($CDCl_3$): 3.38 (m), 3.64 (m). Anal Calcd. for $C_7H_4F_{10}N_4O_5S$: C, 18.84; H, 0.90; N, 12.56; F, 42.58; S, 7.19. Found: C, 18.95; H, 0.94; N, 12.74; F, 36.74; S, 6.58.

EXAMPLE 11

N-(4-Pentafluorothioperfluorobutyryl)-N'-(pentafluorothioacetyl)hydrazine (5A)

To N-(4-pentafluorothioperfluorobutyryl)hydrazine (1.0 g, 0.003 mole) stirred in 30 ml of diethyl ether at 25° C. was added pentafluorothioacetyl chloride (0.75 g, 0.0036 mole) followed by 0.4 ml (0.005 mole) of pyridine (dropwise). After 10 minutes, 10 ml of 10% hydrochloric acid was added and the ether layer was separated, dried ($Na_2SO_4$) and the volatiles were removed. The solid residue was washed with water and then crystallized twice from 1,2-dichloroethane to give 0.93 g (62%) of N-(4-pentafluorothioperfluorobutyryl)-N'-(pentafluorothioacetyl)hydrazine, mp 115°–117° C.; $^1H$ NMR (acetone-$d_6$): 4.76 (pentuplet); IR (KBr): 3280 (NH), 1755, 1710, 1670 (C=O), 1240–1155 (CF), 930–790 ($SF_5$).

EXAMPLE 12

2-(3-Pentafluorothioperfluoropropyl)-5-(pentafluorothiomethyl)-1,3,4-oxadiazole (5)

Phosphorus oxychloride (5 ml) containing 0.5 g (0.001 mole) of N-(4-pentafluorothioperfluorobutyryl)-N'-(pentafluorothioacetyl)hydrazine was held at reflux for 4.5 hours before the mixture was cooled and poured into water to give 0.4 g (83%) of solid, mp 40°–42° C. Chromatography on Silica gel 40 ($CH_2Cl_2$ as eluent) gave purified 2-(3-pentafluorothioperfluoropropyl)-5-(pentafluorothiomethyl)-1,3,4-oxadiazole, mp 42°–44° C.

Anal Calcd for $C_6H_2F_{16}N_2OS_2$: C, 14.82; H, 0.41; F, 62.52; N, 5.76; S, 13.19. Found: C, 14.76; H, <0.5; F, 62.23; N, 5.90; S, 2.67.

EXAMPLE 13

2 N-(3-Pentafluorothioperfluoropropionyl)-N'-(pentafluorothioacetyl)hydrazine (6A)

To a mixture containing 0.90 g (0.0031 mole) of N-(3-pentafluorothioperfluoropropionyl)hydrazine and 0.7 g (0.0034 mole) of pentafluorothioacetyl chloride in 25 ml of diethyl ether stirred at 25° C. was added 0.3 ml (0.0038 mole) of pyridine dropwise. After 10 minutes, dilute hydrochloric acid was added and the ether layer was separated and dried ($Na_2SO_4$) before the volatiles were removed. The residue was stirred with water and then with dichloromethane to give 0.9 g (64%), mp 147°–153° C. Crystallization from 1,2-dichloroethane gave 0.75 g of N-(3-pentafluorothioperfluoropropionyl)-N'-(pentafluorothioacetyl)hydrazine, mp 152°–153° C.; $^1H$ NMR (acetone-$d_6$): 4.77 (pentuplet).

EXAMPLE 14

2-(2-Pentafluorothioperfluoroethyl)-5-(pentafluorothiomethyl)-1,3,4-oxadiazole (6)

A mixture of 0.50 g (0.0011 mole) of N-(3-pentafluorothio perfluoropropionyl)-N'-(pentafluoroacetyl)hydrazine and 5 ml of phosphorus oxychloride was held at reflux temperature for 4.5 hours before it was cooled and poured onto ice to give an insoluble liquid. The liquid was extracted into dichloromethane and chromatographed on Silica gel 40 ($CH_2Cl_2$ as eluent) to give 0.35 g (73%) of 2-(2-pentafluorothioperfluoroethyl)-5-(pentafluorothiomethyl)-1,3,4-oxadiazole, mp 27°–29° C.; $^1H$ NMR (acetone-$d_6$): 5.90 (pentuplet).

Anal. Calcd. for $C_5H_2F_{14}N_2OS_2$: C, 13.77; H, 0.46; F, 60.98; N, 6.42; S, 14.70. Found: C, 13.94; H, <0.5; F, 60.30; N, 6.48; S, 14.25.

EXAMPLE 14

N-(Pentafluorothioacetyl)-N'-(4,4,4-trinitrobutyryl)hydrazine (7A)

A solution containing 4.0 g (0.02 mole) of methyl pentafluorothioacetate and 0.66 g (0.02 mole) of hydrazine (95% minimum) in methanol (17 ml) was stirred at 0° C. for 1 hour. It was then held at room temperature for 2.5 hours until the solution was only slightly basic to damp pH paper. (Gas evolution occurred during the reaction period). An insoluble solid (0.4 g) was removed before the volatiles were evaporated under reduced pressure to give a liquid residue. The amount of $SF_5CH_2C(O)NHNH_2$ in the residue was small as determined by $^1H$ NMR (pentuplet at 4.35 ppm in $CDCl_3$) and a low yield was indicated. To a stirred solution of the residue in 30 ml of diethyl ether was added 2.0 g (0.0083 mole) of 4,4,4-trinitrobutyryl chloride in 8 ml of dichloromethane followed by the dropwise addition of pyridine until the solution was no longer acidic to damp pH paper. Dilute hydrochloric acid was added and the organic layer was separated and dried ($Na_2SO_4$). Removal of volatiles gave 2.8 g which was stirred with dilute aqueous sodium bicarbonate to give an insoluble solid (1.75 g). Crystallization of the solid from dichloromethane gave 1.25 g (15%) of N-(pentafluorothioacetyl)-N'-(4,4,4-trinitrobutyryl)hydrazine, mp 176°-177° C. dec., $^1H$ NMR (acetone-$d_6$): 2.93 (t, 2H), 3.83 (t, 2H), 4.72 (pentuplet, 2H). IR (KBR): 3230 (NH), 1710, 1640 (C=O), 1605 ($NO_2$), 900–800 ($SF_5$).

Anal. Calcd for $C_6H_8F_5N_5O_8$: C, 17.78; H, 1.99; F, 23.44; N, 17.28; S, 7.91. Found: C, 17.91; H, 1.97; F, 23.27; N, 17.47; S, 8.42.

EXAMPLE 16

2-(Pentafluorothiomethyl)-5-(3,3,3-trinitropropyl)-1,3,4-oxadiazole (7)

A mixture of 0.10 g (0.247 mmole) of N-(pentafluorothioacetyl)-N'-(4,4,4-trinitrobutyryl)hydrazine and 1.5 ml of phosphorus oxychloride was held at reflux temperature for 4 hours before it was cooled and poured into water to give 0.07 g of solid, mp 66°-69° C. Crystallization from dichloromethane-hexanes (Silica gel 60 used to remove some brown color) gave 0.05 g (52%) of 2-pentafluorothiomethyl-5-(3,3,3-trinitropropyl)-1,3,4-oxadiazole, mp 72°-73° C. $^1H$ NMR (acetone-$d_6$): 3.70 (m, 2H), 4.20 (m, 2H), 5.63 (pentuplet, 2H). IR (KBr): 1620–1595 ($NO_2$), 895–805 ($SF_5$).

Anal Calcd. for $C_6H_6F_5N_5O_7S$: C, 18.61; H, 1.56; F, 24.53; N, 18.09; S, 8.28. Found C, 18.71; H, 1.57; F, 22.63; N, 17.50; S, 8.76.

An attempt to prepare 2-pentafluorothiomethyl-5-(3,3,3-trinitropropyl)-1,3,4-oxadiazole using phosphorus pentachloride in 1,2-dichloroethane (similar to examples 4 and 6) gave instead the dichloride compound, $SF_5CH_2C(Cl)=N-N=C(Cl)CH_2CH_2C(NO_2)_3$, mp 35°-37° C. $^1H$ NMR (acetone-$d_6$) 3.52 (m, 2H), 4.10 (m, 2H), 5.28 (pentuplet, 2H).

Anal. Calcd. for $C_6H_6Cl_2F_5N_5O_6S$: c, 16.30; H, 1.37; F, 21,49; N, 15.84; S, 7.25. Found: C, 16.82; H, 1.55; F, 18.96; N, 16.09; S, 7.23.

EXAMPLE 17

N-(Pentafluorothioacetyl)-N'-(perfluorobutyryl)hydrazine (9A)

A mixture of 1.1 g (0.0054 mole) of pentafluorothioacetyl chloride and 1.1 g (0.0048 mole) of N-(perfluorobutyryl) hydrazine in 30 ml of diethyl ether was stirred at 25° C. during the dropwise addition of 0.5 ml (0.006 mole) of pyridine. After 5 minutes, dilute hydrochloric acid was added and the ether layer was separated and dried ($Na_2SO_4$). Removal of volatiles and stirring the residue with water gave 1.9 g of solid (mp 140°–145° C.), which was crystallized from 1,2-dichloroethane to yield 1.3 g (68%) of N-(pentafluorothioacetyl)-N'-(perfluorobutyryl)hydrazine, mp 158°-159° C.; $^1H$ NMR (acetone-$d_6$): 4.78 (pentuplet).

EXAMPLE 18

2-(Pentafluorothiomethyl)-5-(perfluoropropyl)-1,3,4-oxadiazole (9)

To 10 ml of phosphorus oxychloride was added 1.0 g (0.0025 mole) of N-(pentafluorothioacetyl)-N'-(perfluorobutyryl)hydrazine and the mixture was held at reflux temperature for 4 hours before it was cooled and poured into water to give an insoluble oil. The oil was extracted into methylene chloride and chromatographed on Silica gel 40 ($CH_2Cl_2$ as eluent) to give 0.5 g (53%) of 2-(pentafluorothiomethyl)-5-(perfluoropropyl)-1,3,4-oxadiazole, mp 28° C.

Anal Calcd. for $C_6H_2F_{12}N_2OS$: C, 19.06: H, 0.53; F, 60.29; N, 7.41; S, 8.48. Found C, 18.62; H, 0.73; F, 60.12; N, 7.70; S, 7.64.

EXAMPLE 19

N,N'-Bis(pentafluorothioacetyl)hydrazine

Hydrazine (0.67 g, 0.02 mole) in methanol (5 ml) was stirred in a dry ice-acetone bath while pentafluorothioacetyl chloride (1.8 g, 0.0088 mole) in ether (3 ml) was added dropwise. After 15 minutes at 0° C., the mixture was poured into water and the insoluble material (0.35 g, mp 271° C. dec) was removed. An additional 0.7 g, mp 270° C. dec was recovered by concentrating the ether solution. Total yield of N,N'-bis(pentafluorothioacetyl)hydrazine is 1.05 g (66%); $^1H$ NMR (acetone-$d_6$): 4.78 (pentuplet); IR (KBr): 3190 (NH), 1635 (C=O), 895°-825 ($SF_5$).

EXAMPLE 20

2,5-Bis(pentafluorothiomethyl)-1,3,4-oxadiazole

N,N'-Bis(pentafluorothioacetyl)hydrazine (0.34 g, 0.92 mmole) in 2.5 ml of phosphorus oxychloride was held at reflux for 4 hours before the solution was cooled and poured into water to give 0.30 g (94%) of 2,5-bis(-pentafluorothiomethyl)-1,3,4-oxadiazole, mp 127°-130° C. Crystallization from dichloromethane gave crystals, mp 128°-130° C. $^1H$ NMR (acetone-$d_6$) 5.54 (pentuplet); IR (KBr): 905-815 ($SF_5$).

Anal. Calcd for $C_4H_4F_{10}N_2OS_2$: C, 13.72; H, 1.15; F, 54.25; N, 8.00; S, 18.31. Found: C, 13.55; H. 1.13; F, 48.66; N, 8.10; S, 18.19.

Numerous other modifications and variations of the present invention are possible in light of the foregoing teachings. It is therefore to be understood that within the scope of the appended claims the invention may be practiced otherwise than as specifically described.

What is claimed is:

1. A 1,3,4-oxadiazole that is
2-(3-pentafluorothioperfluoropropyl)-5-(3,3,3-trinitropropyl)-1,3,4-oxadiazole,
2-(2-pentafluorothioperfluoroethyl)-5-(3,3,3-trinitropropyl)-1,3,4-oxadiazole,
2-(3-pentafluorothioperfluoropropyl)-5-(3-fluoro-3,3-dinitropropyl)-1,3,4-oxadiazole,
2-(2-petafluorothioperfluoroethyl)-5-(3-fluoro-3,3-dinitropropyl)-1,3,4-oxadiazole,
2-(3-pentafluorothioperfluoropropyl)-5-(pentafluorothiomethyl)-1,3,4-oxadiazole,
2-(2-pentafluorothioperfluoroethyl)-5-(pentafluorothiomethyl)-1,3,4-oxadiazole,
2-(pentafluorothiomethyl)-5-(3,3,3-trinitropropyl)-1,3,4-oxadiazole,
2-(pentafluorothiomethyl)-5-(3-fluoro-3,3-dinitropropyl)-1,3,4-oxadiazole,
2-(pentafluorothiomethyl)-5-(perfluoropropyl)-1,3,4-oxadiazole,
2-(pentafluorothiomethyl)-5-(perfluoroethyl)-1,3,4- or
2-(pentafluorothiomethyl)-5-(trifluoromethyl)-1,3,4-oxadiazole.

2. The 1,3,4-oxadiazole of claim 1 that is 2-(3-pentafluorothioperfluoropropyl)-5-(3,3,3-trinitropropyl)-1,3,4-oxadiazole,
2-(2-pentafluorothioperfluoroethyl)-5-(3,3,3-trinitropropyl)-1,3,4-oxadiazole,
2-(3-pentafluorothiolperfluoropropyl)-5-(3-fluoro-3,3-dinitropropyl)-1,3,4-oxadiazole,
2-(2-pentafluorothioperfluoroethyl)-5-(3-fluoro-3,3-dinitropropyl)-1,3,4-oxadiazole,
2-(pentafluorothiomethyl)-5-(3,3,3-trinitropropyl)-1,3,4-oxadiazole, or
2-(pentafluorothiomethyl)-5-(3-fluoro-3,3-dinitropropyl)-1,3,4-oxadiazole.

3. The 1,3,4-oxadiazole of claim 2 which is 2-(3-pentafluorothioperfluoropropyl)-5-(3,3,3-trinitropropyl)-1,3,4-oxadiazole.

4. The 1,3,4-oxadiazole of claim 2 which is 2-(2-pentafluorothioethyl)-5-(3,3,3-trinitropropyl)-1,3,4-oxadiazole.

5. The 1,3,4-oxadiazole of claim 2 which is 2-(3-pentafluorothioperfluoropropyl)-5-(3-fluoro-3,3-dinitropropyl)-1,3,4-oxadiazole.

6. The 1,3,4-oxadiazole of claim 2 which is 2-(2-pentafluorothioperfluoroethyl)-5-(3-fluoro-3,3-dinitropropyl)-1,3,4-oxadiazole.

7. The 1,3,4-oxadiazole of claim 2 which is 2-(pentafluorothiomethyl)-5-(3,3,3-trinitropropyl)-1,3,4-oxadiazole.

8. The 1,3,4-oxadiazole of claim 2 which is 2-(pentafluorothiomethyl)-5-(3-fluoro-3,3-dinitropropyl)-1,3,4-oxadiazole.

* * * * *